(12) United States Patent
Goetz

(10) Patent No.: US 7,035,690 B2
(45) Date of Patent: Apr. 25, 2006

(54) HUMAN-IMPLANTABLE-NEUROSTIMULATOR USER INTERFACE HAVING MULTIPLE LEVELS OF ABSTRACTION

(75) Inventor: Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 623 days.

(21) Appl. No.: 10/295,752

(22) Filed: Nov. 15, 2002

(65) Prior Publication Data

US 2004/0098063 A1 May 20, 2004

(51) Int. Cl.
*A61N 1/18* (2006.01)

(52) U.S. Cl. ............................. 607/46; 607/2; 607/59; 607/60; 349/169; 128/897

(58) Field of Classification Search ................ 607/2, 607/59–60, 46, 154–156; 128/897; 345/169
See application file for complete search history.

(56) References Cited

U.S. PATENT DOCUMENTS

| | | | |
|---|---|---|---|
| 4,328,809 A * | 5/1982 | Hirschowitz et al. ....... 600/407 |
| 4,735,204 A | 4/1988 | Sussman et al. | |
| 5,370,672 A | 12/1994 | Fowler et al. | |
| 5,443,486 A | 8/1995 | Hrdlicka et al. | |
| 5,626,629 A | 5/1997 | Faltys et al. | |
| 5,643,330 A | 7/1997 | Holsheimer et al. | |
| 5,724,985 A * | 3/1998 | Snell et al. ................. 600/510 |
| 5,740,037 A | 4/1998 | McCann et al. | |
| 5,769,875 A | 6/1998 | Peckham | |
| 5,776,171 A | 7/1998 | Peckham | |
| 5,893,883 A | 4/1999 | Torgerson et al. | |
| 5,895,416 A * | 4/1999 | Barreras et al. ............. 607/62 |
| 5,938,690 A | 8/1999 | Law et al. | |
| 5,954,758 A | 9/1999 | Peckham | |
| 6,026,328 A | 2/2000 | Peckham | |
| 6,027,456 A | 2/2000 | Feler et al. | |
| 6,052,624 A | 4/2000 | Mann | |
| 6,077,223 A | 6/2000 | Satherley | |
| 6,099,479 A | 8/2000 | Christopherson et al. | |
| 6,120,467 A | 9/2000 | Schallhorn | |
| 6,163,725 A | 12/2000 | Peckham | |
| 6,208,894 B1 | 3/2001 | Schulman et al. | |
| 6,249,703 B1 | 6/2001 | Stanton et al. | |
| 6,289,247 B1 | 9/2001 | Faltys et al. | |

(Continued)

FOREIGN PATENT DOCUMENTS

EP 0811395 12/1997

(Continued)

*Primary Examiner*—Carl Layno
*Assistant Examiner*—Shevon Johnson
(74) *Attorney, Agent, or Firm*—Banner & Witcoff, Ltd.

(57) ABSTRACT

A programming-device user interface may include multiple levels of abstraction for programming treatment settings. A stimulation zone-programming interface may be at a highest level of abstraction and may include idealized stimulation zones. A field strength-programming interface may be at a middle level of abstraction and may include electromagnetic field-strength patterns generated by the stimulation zones, and/or electrode settings, and a depiction of how the electromagnetic fields interact with each other. An electrode-programming interface may be at a lowest level of abstraction and may depict treatment settings at an electrodes-view level. These interfaces may include a display of a stimulatable area of the patient's body. The display may include a depiction of leads and/or the underlying physiology, such as a depiction of a portion of a spine. Algorithms map treatment settings from one level of abstraction to settings at one or more other levels of abstraction.

28 Claims, 9 Drawing Sheets

U.S. PATENT DOCUMENTS

| | | |
|---|---|---|
| 6,308,102 B1 | 10/2001 | Sieracki et al. |
| 6,381,496 B1 | 4/2002 | Meadows et al. |
| 6,393,325 B1 | 5/2002 | Mann et al. |
| 6,477,424 B1 | 11/2002 | Thompson et al. |
| 6,564,104 B1 | 5/2003 | Nelson et al. |
| 6,574,503 B1 | 6/2003 | Ferek-Petric |
| 6,587,724 B1 | 7/2003 | Mann |
| 6,609,031 B1 | 8/2003 | Law et al. |
| 6,609,032 B1 | 8/2003 | Woods et al. |
| 6,622,048 B1 | 9/2003 | Mann et al. |
| 6,873,872 B1 * | 3/2005 | Gluckman et al. ............. 607/2 |
| 2001/0007950 A1 | 7/2001 | North et al. |
| 2002/0038137 A1 | 3/2002 | Stein |
| 2002/0044059 A1 | 4/2002 | Reeder et al. |
| 2002/0065686 A1 | 5/2002 | Monteleone et al. |
| 2002/0072785 A1 | 6/2002 | Nelson et al. |
| 2002/0095098 A1 | 7/2002 | Marinello |
| 2002/0103512 A1 | 8/2002 | Echauz et al. |
| 2002/0116036 A1 | 8/2002 | Daignault |
| 2002/0120188 A1 | 8/2002 | Brock et al. |
| 2003/0040291 A1 | 2/2003 | Brewer |
| 2003/0158587 A1 | 8/2003 | Esteller et al. |
| 2003/0171789 A1 | 9/2003 | Malek et al. |
| 2003/0174066 A1 | 9/2003 | Goetz et al. |
| 2003/0174069 A1 | 9/2003 | Goetz et al. |
| 2003/0176906 A1 | 9/2003 | Lee |
| 2004/0059395 A1 | 3/2004 | North |

FOREIGN PATENT DOCUMENTS

| | | |
|---|---|---|
| EP | 1134003 | 9/2001 |
| EP | 0939661 B1 | 8/2002 |
| WO | WO 92/17240 | 10/1992 |
| WO | WO 98/43701 | 10/1998 |
| WO | WO 99/56820 | 11/1999 |
| WO | WO 00/02623 | 1/2000 |
| WO | WO 01/39831 | 6/2001 |
| WO | WO 01/43818 | 6/2001 |
| WO | WO 01/47411 | 7/2001 |
| WO | WO 01/80732 | 11/2001 |
| WO | WO 01/93952 | 12/2001 |
| WO | WO 01/93953 | 12/2001 |
| WO | WO 02/01387 | 1/2002 |
| WO | WO 02/34331 | 5/2002 |
| WO | WO 02/39250 | 5/2002 |
| WO | WO 02/47760 | 6/2002 |
| WO | WO 02/49500 | 6/2002 |
| WO | WO 03/037430 | 5/2003 |
| WO | WO 03/077993 | 9/2003 |
| WO | WO 03/077995 | 9/2003 |

* cited by examiner

HUMAN-IMPLANTABLE-NEUROSTIMULATOR USER INTERFACE HAVING MULTIPLE LEVELS OF ABSTRACTION

TECHNICAL FIELD

The invention relates generally to a medical-device user interface and more particularly to such a user interface having multiple levels of abstraction.

BACKGROUND OF THE INVENTION

Medical devices are commonly used today to treat patients suffering from various ailments. Implantable medical devices can be used to treat conditions such as pain, incontinence, movement disorders, such as epilepsy and Parkinson's disease, and sleep apnea. Additionally, use of medical devices appears promising to treat a variety of physiological, psychological, and emotional conditions.

One type of medical device is an Implantable Pulse Generator (IPG). An IPG may be implanted within a patient's body. The IPG may then generate and deliver electrical stimulation signals to influence selected neural tissue to treat a particular ailment. The stimulation sites may include the spinal cord, brain, body muscles, peripheral nerves, or other sites selected by a physician. For example, in the case of pain, electrical impulses may be directed to particular nerves associated with specific sites where the patient is feeling pain. Neurostimulation can give patients effective pain relief and can reduce or eliminate the need for repeat surgeries and pain medications.

An IPG system may include an implantable pulse generator, a programming device, and at least one electrical lead. The IPG may be powered by an internal source such as a rechargeable or non-rechargeable battery or by an external source such as a radio frequency transmitter. The IPG generates and sends precise, electrical pulses to the stimulation area to provide the desired treatment therapy.

The programming device may be an external device that allows a physician and/or patient to communicate with the IPG. A physician may create and store stimulation therapy programs to be administered to the patient by the IPG. The programming device may communicate bi-directionally with the IPG, via RF telemetry signals.

Programming of IPGs has traditionally been done from the hardware level up. For instance, setting amplitudes for particular electrodes that would result in some type of stimulation pattern. Conventional programming-device user interfaces typically do not display a stimulation pattern generated by particular electrode settings. Physicians may not be comfortable thinking about stimulation in terms of electrodes programmed as cathodes and anodes. Further, when there are more than one or two cathode/anode pairs, it becomes relatively difficult to think about how the various electromagnetic fields may interact. There are transverse elements where dipoles affect other dipoles, and the like.

Further, a physician using a conventional user interface to try to optimize therapy settings typically a programming device in one hand and an x-ray or fluoroscopy of the intended stimulation area in the other hand. The x-ray or fluoroscopy shows where the leads are relative to the intended stimulation site, such as the patient's spine. A physician typically knows where nerves come out of a patient's spine and lead to particular areas of the patient's body. So, to treat pain, for instance, the physician is typically trying to arrange the electrodes near those locations of the spine. Accordingly, an interface that shows where leads are placed within the patient's body and that presents a view of stimulation patterns generated by various electrodes settings would be desirable.

SUMMARY OF THE INVENTION

In accordance with an illustrative embodiment of the invention and as described in more detail below, a programming-device user interface may include multiple levels of abstraction. A highest level of abstraction, referred to as a stimulation zone-programming interface, may show idealized stimulation zones. A middle level of abstraction, referred to as a field strength-programming interface, may show electromagnetic fields generated by the stimulation zones, and/or electrode settings, and how these electromagnetic fields interact with each other. A lowest level of abstraction, referred to as an electrode-programming interface, may depict treatment settings at an electrodes-view level. These interfaces may include a display of a stimulatable area of the patient's body. The various forms of this type of display may be referred to herein as a stimulation-zones view, a field-strength view, and an electrodes view, respectively.

A stimulation zone-programming interface, in accordance with an illustrative embodiment of the invention, is relatively simple to interact with and is at a relatively high level of abstraction. The stimulation zone-programming interface lets a user work abstractly with idealized stimulation zones. A user may add a stimulation zone and may move the stimulation zone to a desired location. The user may adjust the stimulation zone's parameters, such as its intensity, its pulse width, and its rate.

A display area of the stimulation zone-programming user interface may represent a stimulatable area within the patient's body, which is an area in which implanted stimulation leads are able to produce stimulation. Before creating idealized stimulation zones, a user may enter information specifying where, within a patient's body, one or more leads are placed, such as where the leads are located relative to specific portions of the patient's spine. Idealized stimulation zones may then be placed relative to placement of the leads.

An image of the underlying physiology of the stimulatable area, such as a portion of the patient's spine, may be displayed based on the lead-location information. The physician may then place stimulation zones relative to the depiction of the stimulatable area's underlying physiology, such as a depiction of the patient's spine.

After programming a first stimulation zone, the physician may add one or more additional stimulation zones and may move the stimulation zones to desired locations. The stimulation zones may be placed in accordance with knowledge of where the nerves, which lead to the arms and legs, come out of the spine. Stimulation zones may be selected, moved, and removed as desired.

Stimulation zones may be placed at predefined locations within the display area, such as at an intersection of a horizontal grid line and a vertical grid line. Intersections of this type may correspond to electrode locations and locations substantially centrally located between an electrode on a first lead and an electrode on a second lead.

A field strength-programming interface, in accordance with an illustrative embodiment of the invention, may be at a level of abstraction lower than the stimulation zone-programming interface and at a level higher than the electrode-programming interface. For a user who is comfortable thinking about electromagnetic fields directly, the user may paint on the user interface what the user wants the field pattern to look like. Darker colors may be used to represent more intensity, for instance.

A field strength-programming interface may show the extent to which an electromagnetic field attributable to one stimulation zone overlaps with one or more additional electromagnetic fields attributable to one or more additional stimulation zones. For instance, if unintended results are occurring for stimulation zones that have been programmed, an electromagnetic-fields view provided by the field strength-programming interface may indicate that the interaction between particular stimulation zones is causing the unintended results. The user may interact with user interface controls to reduce the interaction between the stimulation zones.

An electrode-programming interface, in accordance with an illustrative embodiment of the invention, may be at a level of abstraction lower than the stimulation zone-programming interface and the field strength-programming interface. Users, who want to specify treatment parameters by specifying electrode settings, may use the electrode-programming interface. If desired, the user may then view resulting electrical fields or current densities that will act on various portions of the stimulatable area by transitioning to a higher level of abstraction, such as the field strength-programming interface.

In accordance with an illustrative embodiment of the invention, for each displayed pixel within a field-strength view's displayed stimulatable area, the contribution from each modeled point charge may be individually calculated and then added together. For each pixel of interest, a field strength may be calculated and then the pixel may be assigned a visual indication, such as a color, based on the calculated field strength.

When an idealized-stimulation-zone pattern is known, steps, in accordance with an illustrative embodiment of the invention, may map either the stimulation zones view or the fields view to the electrodes view by generating electrode settings that approximate the known stimulation-zones pattern. The stimulation zones may be mapped to electrode settings via a successive-approximation technique. Starting with a strongest stimulation zone and working to successively weaker stimulation zones, an electrode pair may be placed as close as possible to the location of the corresponding stimulation zone.

In accordance with an illustrative embodiment of the invention, an electromagnetic fields-view representation of stimulation zones may be mapped to an electrodes interface, when an electromagnetic-fields representation is known, but a corresponding pattern of idealized stimulation zones is unknown. An approximation of a set of idealized stimulation zones may be generated via successive approximations that will attempt to approximate the known electromagnetic-fields pattern. An area, which has the highest intensity among areas not corresponding to an already-placed stimulation zone, is found and a stimulation zone is placed at the found area. After placing a stimulation zone in this manner, a field-strength pattern is calculated based on any stimulation zones that have already been placed. A determination is then made as to whether the calculated field pattern, which is based on the stimulation zones placed so far, is a sufficient approximation of the desired fields. If the placed stimulation zones do not sufficiently approximate the desired field-strength pattern, then an attempt is made to place at least one additional stimulation zone in a similar manner.

Additional features and advantages of the invention will be apparent upon reviewing the following detailed description.

DETAILED DESCRIPTION OF THE INVENTION

Figure 1:
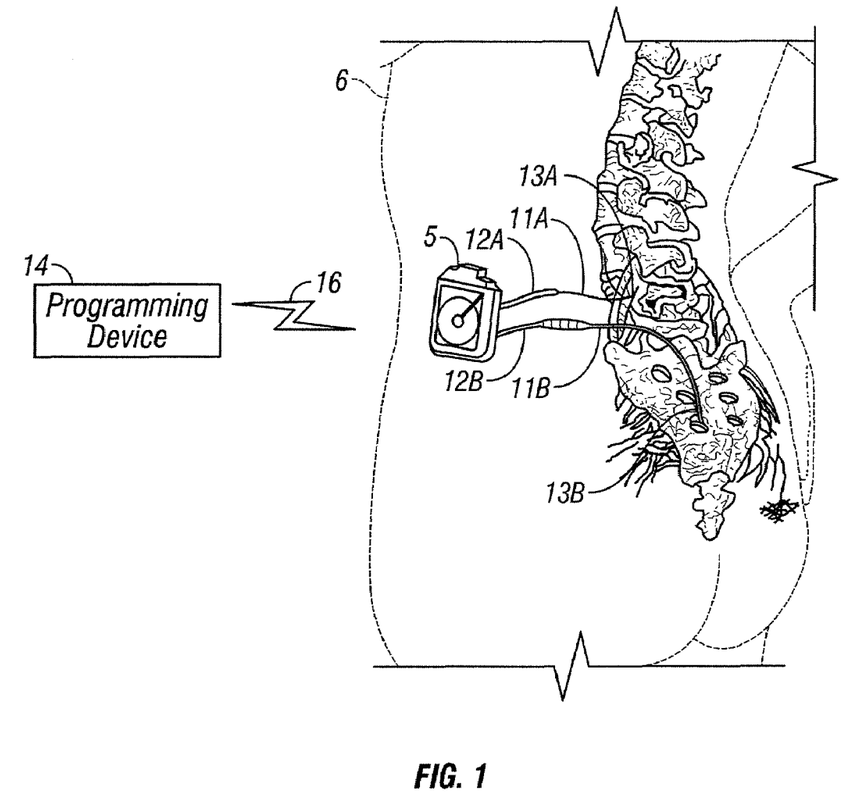
FIG. 1 depicts an exemplary operating environment for programming neurostimulation-treatment parameters via a user interface in accordance with an illustrative embodiment of the invention.

FIG. 1 shows a general environment where a medical device such as an Implantable Pulse Generator (IPG) 5 may be used within a patient 6. The IPG 5 may contain a power source and electronics to send precise, electrical pulses to the spinal cord, brain, or other neural tissue to provide a desired treatment therapy. The IPG 5 may be powered by an internal source such as a rechargeable or non-rechargeable battery or by an external source such as a radio frequency transmitter. The IPG 5 may provide electrical stimulation by way of electrical pulses. Other forms of stimulation, however, may be used such as continuous electrical stimulation.

The IPG 5 may use one or more leads 11A and 11B, and optionally extensions 12A and 12B, for delivering therapy. The leads 11A and 11B may be surgically implanted within the patient 6. The leads 11A and 11B may be implanted and positioned to stimulate a specific site or area. The leads 11A and 11B may be positioned along a peripheral nerve, adjacent neural tissue, near muscle tissue or at other stimulation sites chosen by a clinician. The leads 11A and 11B contain one or more electrodes (small electrical contacts) 13A and 13B through which electrical stimulation may be delivered from the IPG 5 to the targeted neural tissue. The electrodes 13A and 13B may be arranged in a predetermined physical layout. For example, where there is more than one electrode, the electrodes may be arranged in a linear array, in multiple linear arrays, or in a particular geometric array such as a triangle, square, rectangle, circle, etc. In addition, the IPG 5 may deliver stimulation therapy signals via the electrodes in a predetermined directional sequence based on the electrodes' physical layout in the stimulation area.

A programming device 14 may be used for programming various treatment parameters of the therapeutic neurostimulation to be administered by the IPG 5. Data, such as the treatment parameters, may be transmitted from the programming device 14 via an RF link 16 to the IPG 5. Similarly, IPG-status information may be transmitted from the IPG 5 to the programming device 14 over the RF link 16.

In accordance with an illustrative embodiment of the invention and as described in more detail below, a programming-device user interface may include multiple levels of abstraction. A highest level of abstraction, referred to as a stimulation zone-programming interface, may show idealized stimulation zones. A middle level of abstraction, referred to as a field strength-programming interface, may show electromagnetic fields generated by the stimulation zones, and/or electrode settings, and how these electromagnetic fields interact with each other. A lowest level of abstraction, referred to as an electrode-programming interface, may depict treatment settings at an electrodes-view level. These interfaces may include a display of a stimulatable area of the patient's body. The various forms of this type of display may be referred to herein as a stimulation-zones view, a field-strength view, and an electrodes view, respectively.

Figure 2:
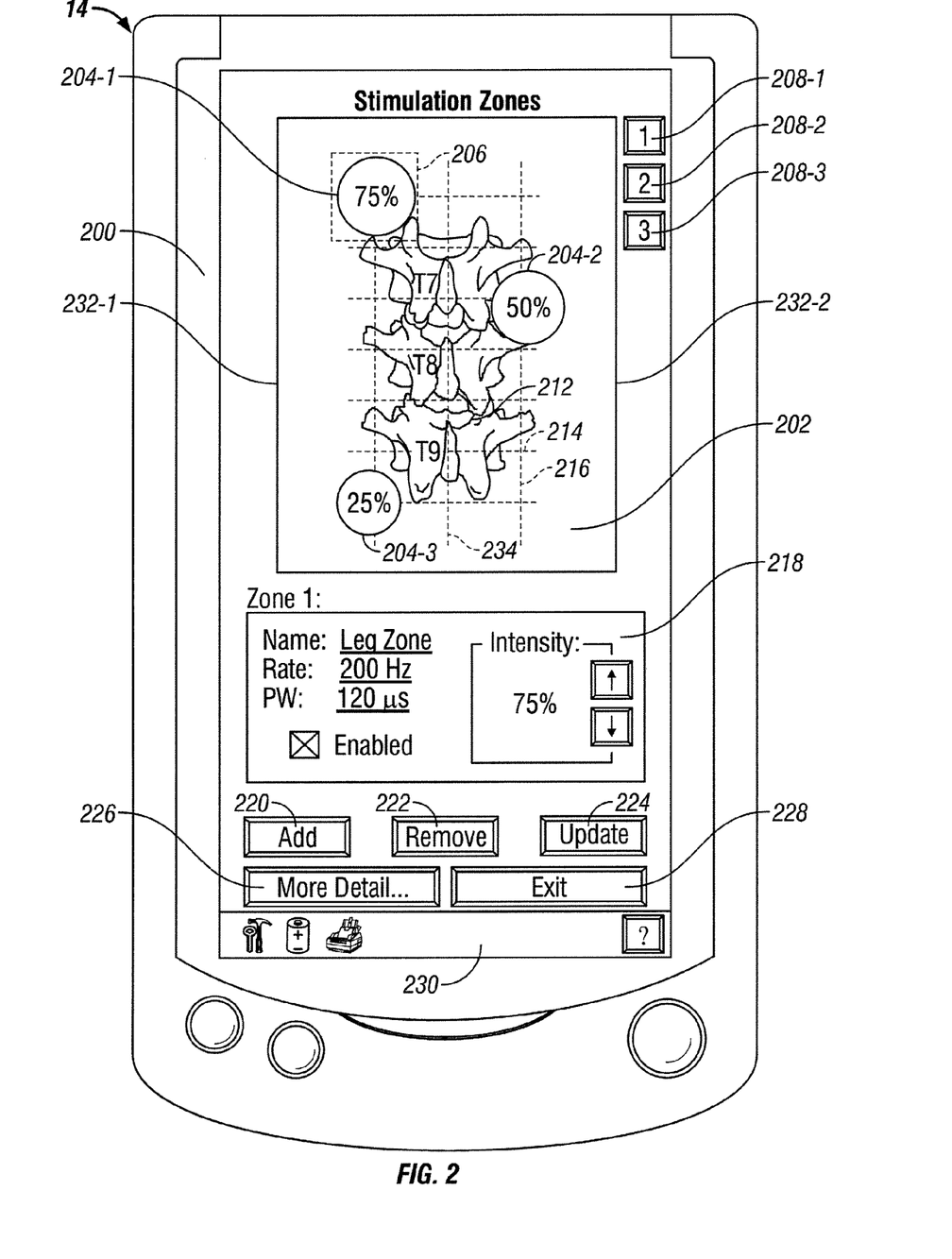
FIG. 2 depicts a stimulation zone-programming interface in accordance with an illustrative embodiment of the invention.

FIG. 2 depicts a stimulation zone-programming interface 200 in accordance with an illustrative embodiment of the invention. This type of interface is relatively simple to interact with and is at a relatively high level of abstraction in accordance with an illustrative embodiment of the invention. The stimulation zone-programming interface 200 lets a user work abstractly with idealized stimulation zones, such as idealized stimulation zones 204-1 through 204-3. These stimulation zones are depicted with relative sizes corresponding to their respective intensities, namely, zone 204-1, with an intensity of 75%, is represented by a large circle; zone 204-2, with an intensity of 50%, is shown with a medium-sized circle; and zone 204-3, with an intensity of 25% is shown with a small circle.

Initially, there may have been no active stimulation zones. A user, such as a physician, may add a stimulation zone and may move the stimulation zone to a desired location. The user may adjust the stimulation zone's parameters, such as its intensity, its pulse width, and its rate, example values of which are displayed in treatment parameter-display area 218. An indication 206 of which stimulation zone is currently selected for programming may be displayed. Zone-selection buttons 208-1 through 208-3 may be provided for selecting a stimulation zone 204 for programming.

A display area 202 of the stimulation zone-programming user interface 200 represents a stimulatable area within the patient's body, which is an area in which implanted stimulation leads are able to produce stimulation. Two leads are often implanted parallel to one another above, and parallel to, a patient's spine. Referring to FIG. 2, a first lead and a second lead correspond to the left and right edges 232-1 and 232-2 of the displayed stimulatable area such that stimulation zones may be placed within in the display area 202. Before creating idealized stimulation zones, a user may enter information specifying where, within a patient's body, one or more leads are placed, such as where the leads are located relative to specific portions of the patient's spine. This type of lead-location information may also be made available by any other suitable technique, such as the programming device 14 querying the IPG 5 for lead-location information.

Idealized stimulation zones may be placed relative to placement of the leads. A common configuration for implanted leads is two leads each with four electrodes in parallel forming a rectangle. The stimulation zones typically will fall somewhere within that rectangle. Using a stimulation-zones view 200, a user may place idealized stimulation zones 204 and configure stimulation parameters such as stimulation-zone intensity. For instance, the user may put a higher intensity stimulation zone, such as stimulation zone 204-1, in the upper left hand portion and a lower intensity stimulation zone, such as idealized stimulation zone 204-2, lower and to the right.

An image 212 of the underlying physiology of the stimulatable area, such as a portion of the patient's spine, may be displayed based on the lead-location information. The physician may then place stimulation zones relative to the depiction 212 of the stimulatable area's underlying physiology, such as a depiction of the patient's spine.

After programming a first stimulation zone, the physician may add one or more additional stimulation zones and may move the stimulation zones to desired locations. For instance, if a first stimulation zone is providing effective pain relief for leg pain and the patient also has arm pain, a second stimulation zone may be added to treat the patient's arm pain. The stimulation zones may be placed in accordance with knowledge of where the nerves, which lead to the arms and legs, come out of the spine. Stimulation zones may be selected, moved, and removed as desired.

Stimulation zones may be placed at predefined locations within the display area 202, such as at an intersection of a horizontal grid line 214 and a vertical grid line 216. Intersections of this type may correspond to electrode locations and locations substantially centrally located between an electrode on a first lead and an electrode on a second lead.

In the lower portion of the stimulation zone-programming interface 200 shown in FIG. 2, the treatment-parameter display area 218 depicts a name, rate, pulse width and intensity of a selected stimulation zone 204. Below the treatment-parameter display area 218 are buttons 220 through 228 and a status bar 230. The buttons may be used for adding (220) or removing (222) a stimulation zone. The update button 224 may be used for transferring programmed settings to the IPG 5. The more-detail button 226 may be used for transitioning from one level of abstraction, such as the stimulation zone-programming interface 200, to a different level of abstraction, such as the field strength-programming interface 300 (FIG. 3) or the electrode programming-interface 400 (FIG. 4).

Figure 3:
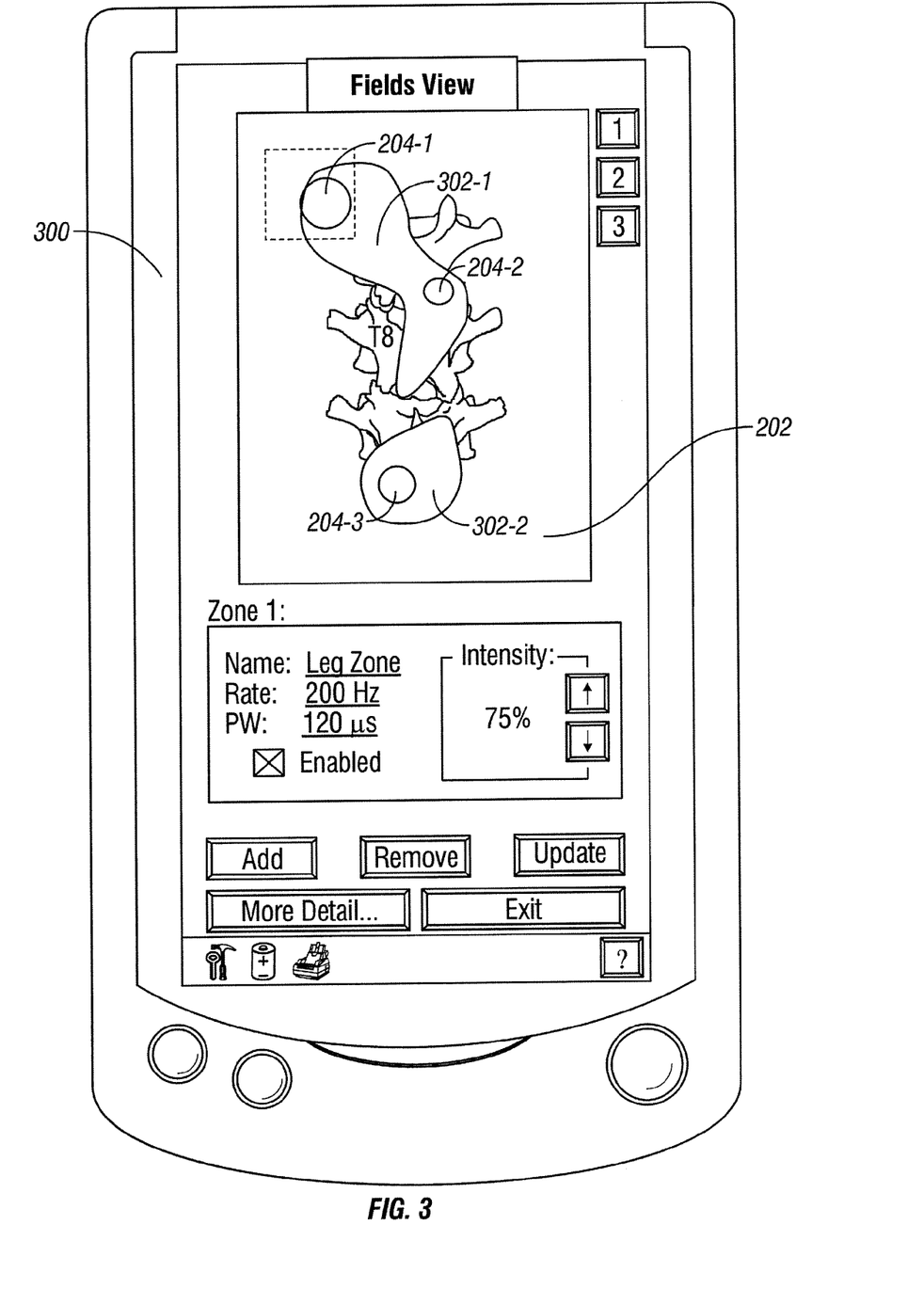
FIG. 3 depicts a field strength-programming interface 300 in accordance with an illustrative embodiment of the invention.
Figure 4:
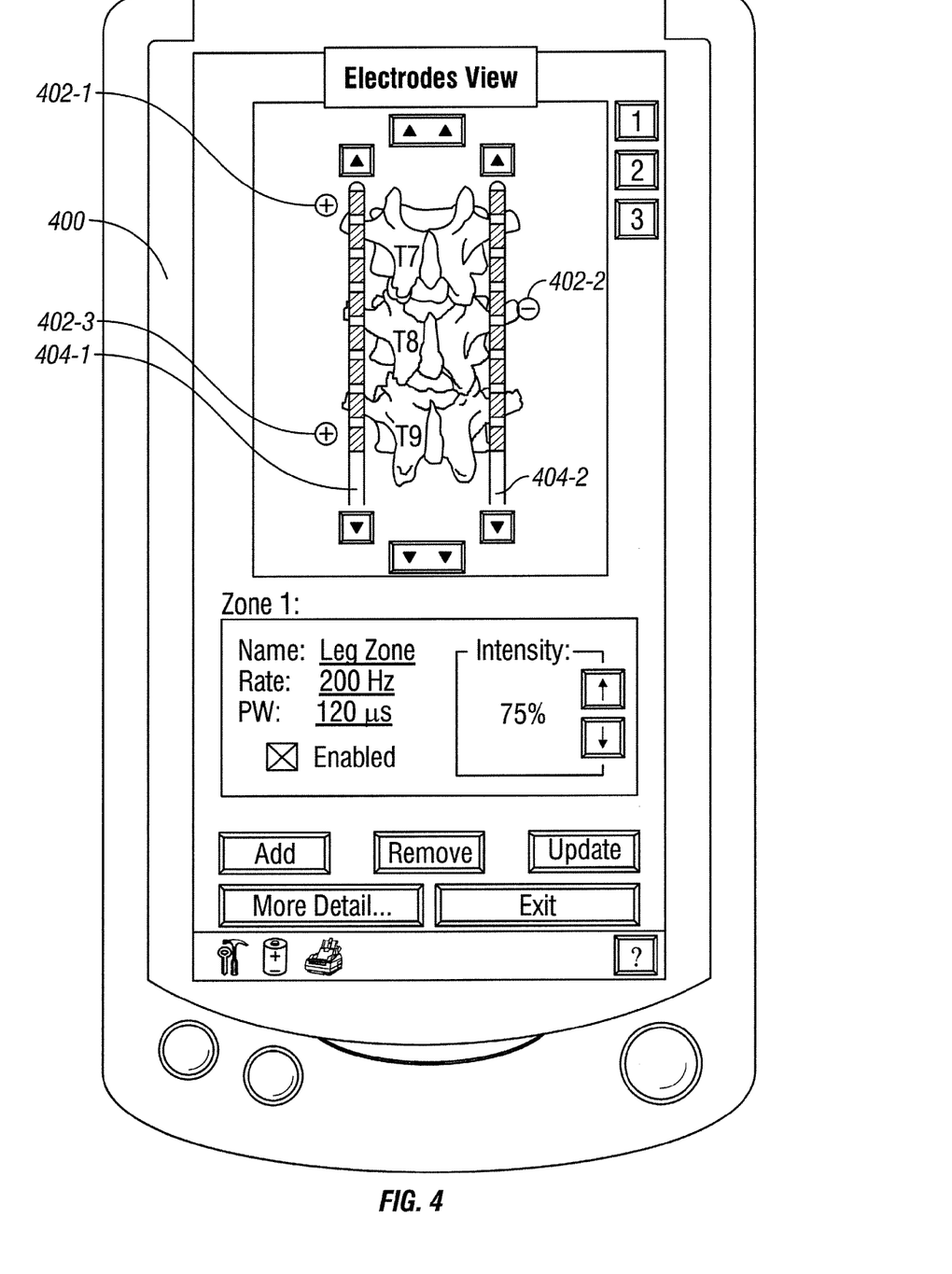
FIG. 4 depicts an electrode-programming interface 400 in accordance with an illustrative embodiment of the invention.

FIG. 3 depicts a field strength-programming interface 300 in accordance with an illustrative embodiment of the invention. This type of interface is, in accordance with an illustrative embodiment of the invention, at a level of abstraction lower than the stimulation zone-programming interface 200 (FIG. 2) and at a level higher than the electrode-programming interface 400 (FIG. 4). For a user who is comfortable thinking about electromagnetic fields directly, the user may paint on the user interface what the user wants the field pattern to look like. Darker colors may be used to represent more intensity, for instance. While the field-strength view of FIG. 3 is less abstract than the idealized stimulation zones view of FIG. 2, the field-strength view of FIG. 3 is more abstract than displaying which electrodes will be activated in what manner on which leads to perform neurostimulation as desired.

In accordance with an illustrative embodiment of the invention, a field-strength view 300 may depict a polarity or direction for various displayed electromagnetic fields. An electromagnetic field may be displayed as a vector having a direction and a magnitude. A user may then adjust not only the magnitude, but also the direction of an electromagnetic field being displayed as a vector.

A field strength-programming interface 300 may show the extent to which an electromagnetic field attributable to one stimulation zone overlaps with one or more additional electromagnetic fields attributable to one or more additional stimulation zones. For instance, if unintended results are occurring for stimulation zones that have been programmed, an electromagnetic-fields view provided by the field strength-programming interface 300 may indicate that the interaction between particular stimulation zones is causing the unintended results. The user may interact with the user interface controls shown in FIG. 3 in a manner similar to the manner discussed above in connection with FIG. 2. The primary difference is that the stimulation zones are displayed in the electromagnetic-fields view in FIG. 3 as opposed to the idealized-stimulation-zones view of FIG. 2. To reduce overlap of fields, as shown in FIG. 3, a user may reduce the intensity of, or move the location of, one or more of the stimulation zones 204.

In accordance with an illustrative embodiment of the invention, the shape of electromagnetic fields 302-1 and 302-2 corresponding to the idealized stimulation zones 204-1 through 204-3 is shown. The strength of the displayed electromagnetic fields may be depicted by relative shading or coloring of the displayed fields to indicate the relative strength of the fields at various locations within the display area 202.

FIG. 4 depicts an electrode-programming interface 400 in accordance with an illustrative embodiment of the invention. This type of interface is, in accordance with an illustrative embodiment of the invention, at a level of abstraction lower than the stimulation zone-programming interface 200 (FIG. 2) and the field strength-programming interface 300 (FIG. 3). Users who want to specify treatment parameters by specifying electrode settings may use the electrode-programming interface 400. If desired, the user may then view resulting electrical fields or current densities that will act on various portions of the stimulatable area by transitioning to a higher level of abstraction, such as the field strength-programming interface 300.

Steps for generating, displaying, and using the stimulation zone-programming interface 200, the field strength-programming interface 300, and the electrode programming interface 400 will now be discussed in connection with FIGS. 5–9.

Figure 5:
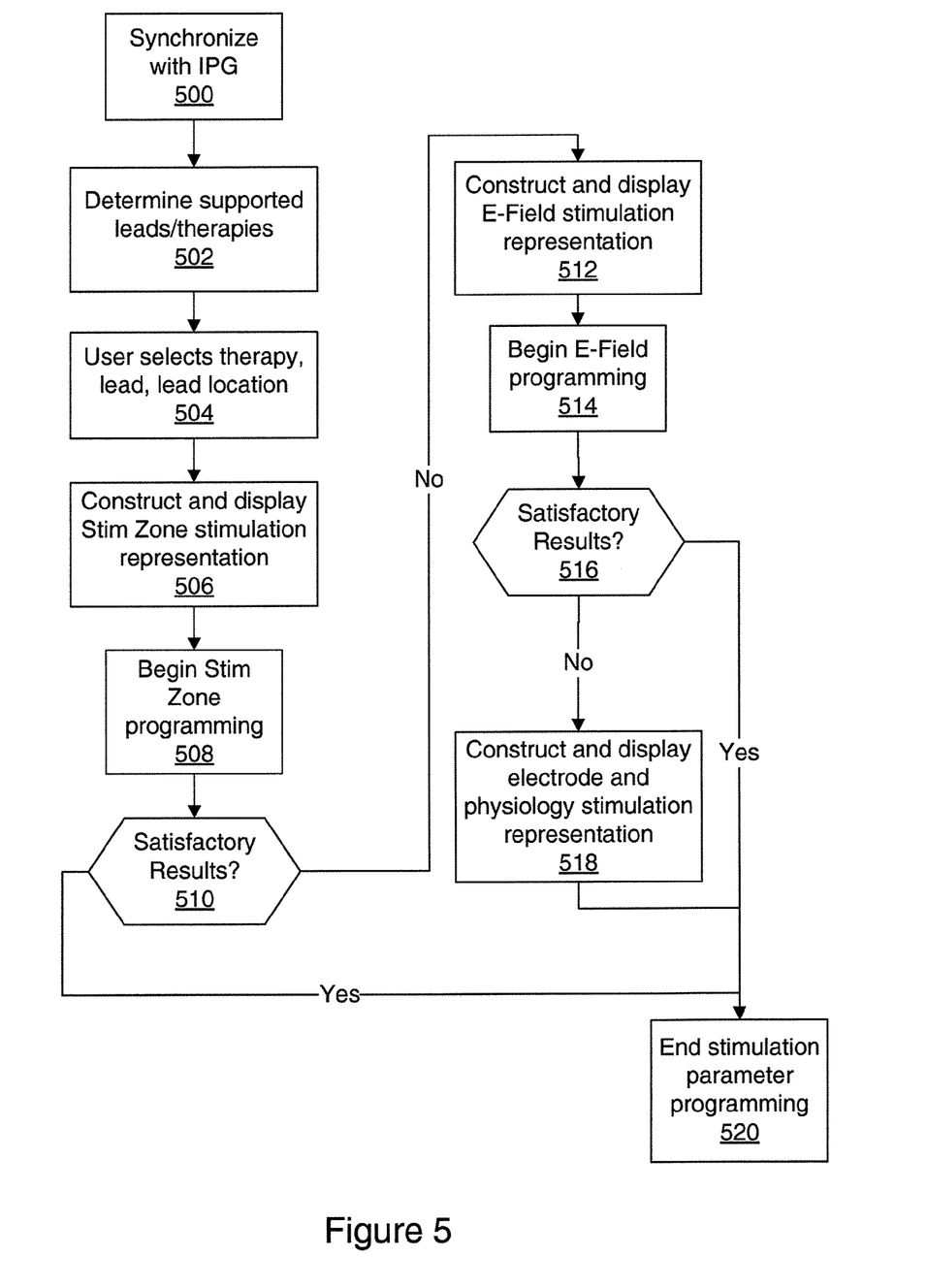
FIG. 5 is a flowchart depicting an overview of steps, in accordance with an illustrative embodiment of the invention, for programming neurostimulation parameters via a user interface having three levels of abstraction.

FIG. 5 is a flowchart depicting an overview of steps, in accordance with an illustrative embodiment of the invention, for programming neurostimulation parameters via a user interface having three levels of abstraction. FIG. 5 depicts an overall task flow of a possible programming session. Although FIG. 5 depicts a single iteration from a highest level of abstraction to a lowest level of abstraction any number of transitions from one level of abstraction to another level of abstraction may be performed, as desired by a user.

As depicted at step 500, the programming device 14 and the IPG 5 may synchronize their data. For instance, the programming device 14 may query the IPG 5 for the IPG's current settings. Different IPGs may differ in the size of their batteries, the number of electrodes, the number of leads, and the like.

As depicted at step 502, a determination is made regarding the type of leads that are present and/or the kind of therapy that may be performed. A particular IPG 5 may be used for one or more therapies, such as pain therapy or deep brain stimulation. Data regarding the type of therapy to be performed may be used in connection with displaying the underlying physiology of the intended stimulation area. For example, the image 212 of the patient's spine shown in FIG. 2 may be appropriate for pain treatment, but not for deep brain stimulation. Similarly, different types of leads may vary in the number of electrodes, the spacing of electrodes, and/or the arrangement of electrodes, such as paddle leads that are smaller and wider than typical leads. This electrode-configuration information may be used in connection with displaying an image the leads, such as the lead images 404-1 and 404-2 shown in FIG. 4.

Configuration information of the type discussed in the immediately preceding paragraph may be queried via telemetry from various types of IPGs 5. Alternatively, this kind of information may be input by a user.

A user may then input lead-location information, as depicted at step 504. For instance, the user could indicate that a lead is implanted at the tip of T7 (i.e., the seventh thoracic vertebra). Or the user may indicate that the lead is located in some structure of the brain. This information may be used in connection with graphically displaying leads superimposed over the stimulation area's underlying physiology. A user may input lead location information by entering a textual description of one or more lead locations. The user could also drag-and-drop a graphic of the lead on to a graphic of the stimulation area, such as a portion of the patient's spine or brain to indicate the lead location graphically. Lead placement relative to the spine may be used for specifying where pain treatment will be directed. For instance, arm pain and leg pain maybe treated with leads located in different areas of the spine where nerves exit the spine and lead to these respective body parts.

As depicted at step 506, a stimulation-zones view may be displayed based on the information discussed above in connection with steps 500–504. For instance, as part of displaying a stimulation-zones view, the following information may be taken into consideration: the capabilities of the stimulator, the type of lead or leads, the type of therapy, and the physiological location of the lead. Based on this type of information, a stimulation-zones view, such as the one shown in FIG. 2, may be constructed and displayed.

A user may then create, specify parameters for, move, and/or delete idealized stimulation zones, as depicted at step 508.

If the user gets satisfactory results at this relatively high level of abstraction, then programming the IPG 5 is complete for the desired treatment, as depicted by following the "yes" branch from step 510 to step 520. If the user does not achieve satisfactory results at this level of abstraction, then the user may go a lower level of abstraction within the user interface, such as an electromagnetic-fields view, like the one shown in FIG. 3.

"Satisfactory results" in step 510 may refer to a subjective indication from the patient. In other words, a qualitative response about the effectiveness of the treatment. The physician may change various stimulation parameters and get feedback from the patient about whether the change improved the effectiveness of the treatment. For instance, the patient might indicate the degree to which pain or any other symptoms are diminished.

As depicted at steps 512 and 514, an electromagnetic-fields view may be constructed, and the user may program various treatment parameters from the electromagnetic-fields view. Step 512 refers to displaying a view such as the electromagnetic-fields view shown in FIG. 3. This type of view may show the extent to which a particular stimulation zone overlaps with one or more additional stimulation zones.

To reduce overlap of fields, as shown in FIG. 3, a user could reduce the intensity of one or more of the stimulation zones. There are also other ways to reduce the overlap of fields. For instance, a user could place an electrode with a negative polarity very close to a positive electrode so that the resulting field would be constrained around those two electrodes. So, instead of creating each zone with a single electrode, a user could set up stimulation zones with two or more electrodes. For instance, a plus-minus-plus triplet or a minus-plus-minus arrangement, which is called a guarded cathode, may be used. Electrodes near a particular electrode may be used to control the manner in which electric fields emanate from the electrode. The lowest level of abstraction, such as the electrodes view of FIG. 4, allows a user to program settings for individual electrodes in this way.

If the user gets satisfactory results at the electromagnetic-fields-view level of abstraction, then programming the IPG is complete for the desired treatment, as depicted by steps 516 and 520. If the user does not achieve satisfactory results at this level of abstraction, then, as depicted at step 518, the user may go to a lower level of abstraction within the user interface, such as an electrodes view, like the one shown in FIG. 4. If satisfactory results are not achieved at the electrodes-view level, then the user may iterate to another level, remove and/or reposition one or more of the leads, and/or make other changes to the system, as appropriate.

Figure 6:
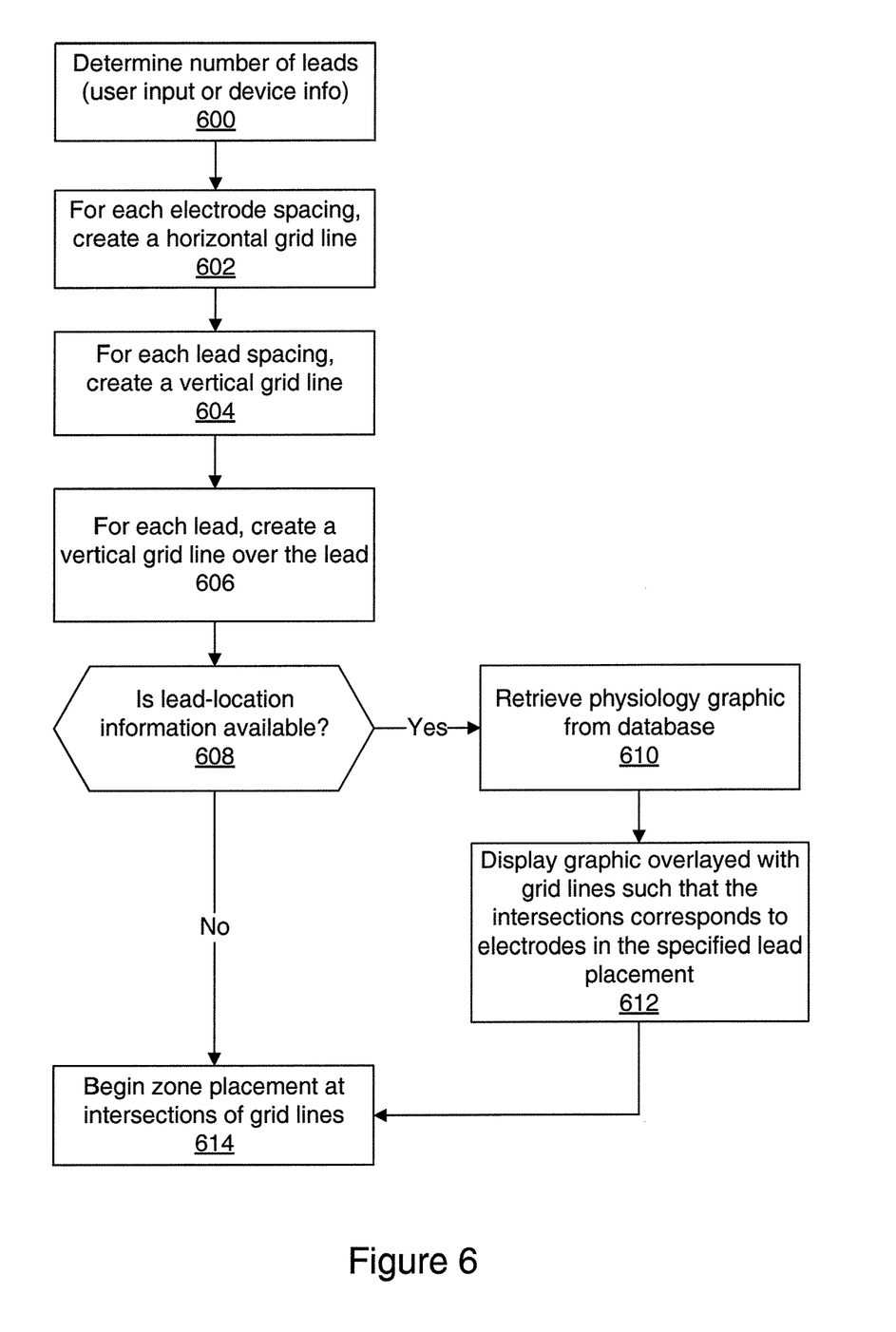
FIG. 6 is a flowchart depicting an overview of construction and display of a stimulation zone-programming interface in accordance with an illustrative embodiment of the invention.

FIG. 6 is a flowchart depicting an overview of construction and display of a stimulation zone-programming interface in accordance with an illustrative embodiment of the invention. Step 600 corresponds to steps 500–504 of FIG. 5. As mentioned previously, the programming device 14 may query the IPG 5 for information, such as the number of leads, or a user may enter this type of information as input.

A visual indication may be displayed for indicating distinct positions at which a user may position idealized stimulation zones. For instance, as depicted at steps 602–606, a grid of vertical and horizontal lines may be drawn on the programming device's display area 202. A vertical line 216 may be drawn substantially over each lead and halfway between adjacent pairs of leads. A horizontal line 214 may be drawn for each electrode. The vertical grid line 234 (FIG. 2) between the electrodes, drawn by step 604, provides a user the option of placing stimulation zones between the leads. For instance, idealized stimulation zone 204-1 could be moved one grid space to the right of its location in FIG. 2 so that the stimulation zone 204-1 was then located on vertical grid line 234. This could be achieved at the electrode-programming level, discussed below, by activating a top most electrode on both leads corresponding to the left and right edges 232-1 and 232-2 of the displayed stimulatable area 202. The resulting field would then be substantially centered between these two electrodes, thereby producing a net result of stimulation in the middle between the electrodes.

In an ideal case, there is a virtually unlimited number of electrodes on a lead, and stimulation zones may be placed in virtually any position within the displayed stimulatable area 202. Conventional leads, however, typically have four or eight electrodes. Accordingly, the resolution of the electrodes effectively places a practical limit on where idealized stimulation zones may be located. Therefore, rather than allowing a user to place a stimulation zone wherever the user wants to, and then requiring the user interface to move the arbitrarily placed stimulation zone to the nearest grid location, the user interface may use the grid to indicate to the user where the stimulation-zones may be located. Use of a grid in this manner may advantageously allow a user to avoid confusion associated with stimulation zones being repositioned without the user's knowledge. Using discrete stimulation-zone locations in this manner also advantageously simplifies the steps performed by the user interface for transitioning from one level of abstraction to a different level of abstraction.

An image of the stimulatable area's underlying physiology, such as an image of a portion of a person's spine, may be depicted, as shown at step 610. Selection of an image to be displayed may be based on available lead-location information.

Figure 7:
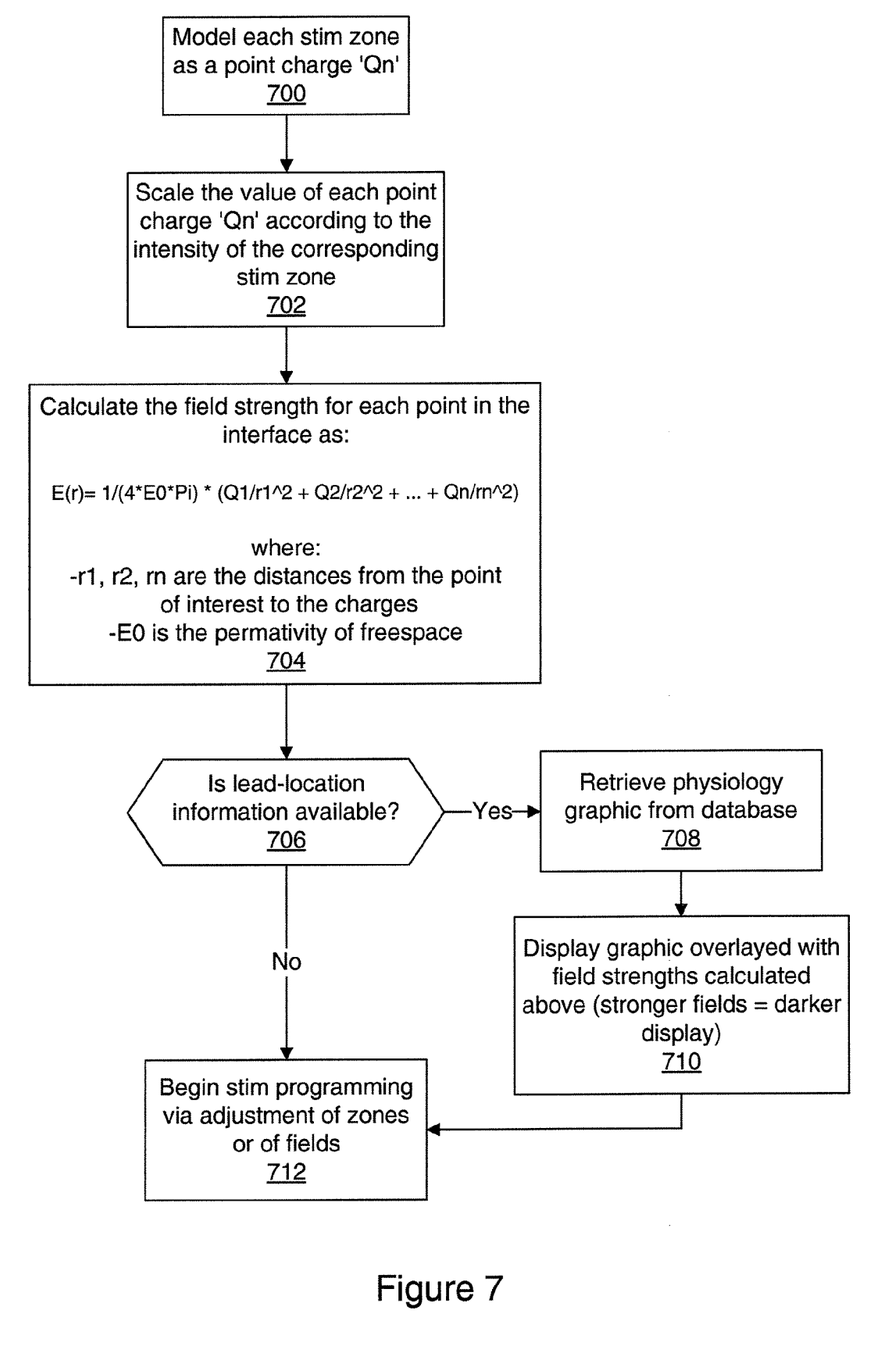
FIG. 7 depicts steps in accordance with an illustrative embodiment of the invention for constructing and displaying a stimulation field strength-programming interface.

FIG. 7 depicts steps in accordance with an illustrative embodiment of the invention for constructing and displaying a stimulation field strength-programming interface 300. The steps in FIG. 7 relate to transitioning from a stimulation-zone interface 200 to a field-strength interface 300. As depicted at step 700, an electromagnetic-field strength for each stimulation zone is modeled as a respective point charge, which is an approximation technique. Alternatively, a finite element analysis could be done. Analytic approaches tend to lead to cylinders of charge. As the number of electrodes to be modeled increases, this type of approach tends to become relatively complex. Modeling the field strength as point charges provides a relatively accurate approximation and the computational complexity is reduced so that a processor may execute the computations more quickly. In addition to finite element analysis, other analytical approaches may include calculating voltages and/or current densities.

At step 702, the modeled point charges are scaled according to the stimulation zones' respective intensities. At step 704, an electromagnetic field is calculated for a desired set of points within a window of interest, which may be the displayed stimulatable area 202. For each displayed pixel within the displayed stimulatable area, the contribution from each modeled point charge may be individually calculated and then added together. There is an inverse-squared relationship between the distance from a point charge and the strength of the electromagnetic field attributable to the point charge. So, for example, as a reference distance is tripled, the strength of the electromagnetic field will reduce by a factor of 9, which is 3 squared.

The algebraic expression in step 704 may be evaluated pixel-by-pixel for each pixel within the displayed stimulatable area. Or this calculation may be performed for any other desired set of points, such as a subset of the pixels within the displayed stimulatable area. For each pixel of interest, a field strength may be calculated and then the pixel may be assigned a visual indication, such as a color, based on the calculated field strength.

On the left the algebraic expression in step 704, is the net field strength $E(r)$ for a pixel at location r, which may be some x-y pixel location. The first term to the right of the equal sign comprises 3 constants and is, therefore, itself a constant. Stated differently, the inverse of four times $E_0$ times p is a constant. $E_0$ is the permativity of free space, which relates to the speed at which light travels in a vacuum. $E_0$ may be varied depending upon the type of material in which the leads have been implanted. Evaluation of the expression proceeds charge-by-charge with $Q1/R1^2$. Q1 is the charge that a first electrode is modeled with. So $Q1/R1^2$ represents a point charge located at a specific pixel location away from where the first electrode is located on the lead, for instance. Q1 may be scaled based on the intensity of the first stimulation zone or electrode being modeled. R1 represents the distance between the point charge being modeled and the current pixel's location. R may be a distance measured in pixels or some other unit of length. So, the further away the pixel is from the electrode being modeled as a point charge, the weaker the electrode's contribution will be to the net field strength at the pixel.

For a particular pixel, each electrode's contribution to the field strength for that pixel is calculated. For instance, $Q2/R2^2$ may represent a second electrode's contribution to the net field strength at the current pixel. For any given calculation, a lot of the electrodes will typically be off so that their Q values will be zero. As indicated in the equation of step 704, the $Q/R^2$ contribution of each electrode is summed to produce a net field strength for a particular displayed pixel.

Steps 706–712 are similar to steps 608–614 described above. If lead-location information is unavailable, for instance, because the user has not entered any or the lead is nonstandard, then stimulation programming may begin, as depicted at step 712, without displaying a depiction of the underlying physiology of the stimulatable area.

Figure 8:
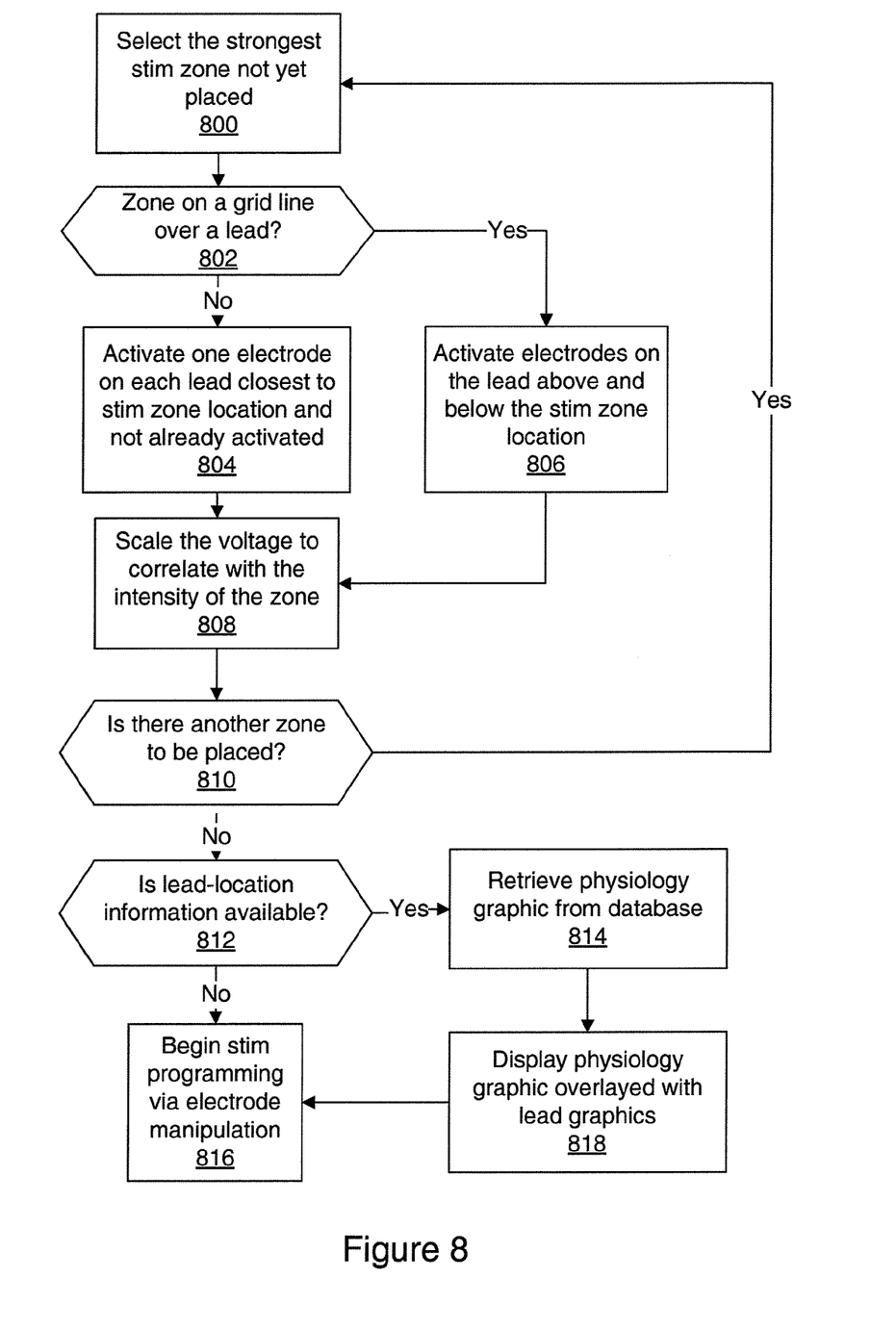
FIG. 8 depicts steps in accordance with an illustrative embodiment of the invention for moving from either the stimulation zones view or a fields view to an electrodes view when an idealized-stimulation-zone pattern is known.

FIG. 8 depicts steps in accordance with an illustrative embodiment of the invention for moving from either the stimulation zones view of FIG. 2 or the fields view of FIG. 3 to the electrodes view of FIG. 4 when an idealized-stimulation-zone pattern is known. In light of the known capabilities of the IPG 5 and any available lead-configuration information, FIG. 8 sets forth steps in accordance with an illustrative embodiment of the invention for generating electrode settings that approximate the known stimulation zones.

To map stimulation zones to electrodes settings, equations for an arbitrary number of electrodes may be written and solved. This type of approach involves relatively complicated calculations. A relatively simpler approach, in accordance with an illustrative embodiment of the invention, essentially approximates what the electrode setting should be for a particular pattern of stimulation zones.

FIG. 8 depicts steps in accordance with an illustrative embodiment of the invention for mapping stimulation zones to electrodes settings via an approach of successive approximations. In general, a stimulation zone comprises two electrodes, a positive cathode and a negative anode. Accordingly, the steps in FIG. 8 place an electrode pair of this type for each stimulation zone. If a stimulation zone is located over one lead, then both electrodes of an electrode pair are placed on that lead. For instance, the two electrodes closest to the stimulation zone, which have not already been activated, may be activated, with one positive and one negative, to generate stimulation corresponding to the stimulation zone. A slightly more difficult case is when the stimulation zone is located between the leads. An electrode on a first lead and an electrode on a second lead may then be used to produce a stimulation zone between the leads.

Starting with a strongest stimulation zone first, as depicted at steps 800–808, a first electrode-pair is generated to produce stimulation approximating the strongest stimulation zone. The first electrode pair may be on a single lead (step 806) or may span two leads (step 804). Whether an electrode pair to be activated will be placed on one lead or across multiple leads may depend upon whether the stimulation zone is located more toward the left, toward the right, or in the center of the displayed stimulatable area 202. The first electrode pair may be set to a midrange voltage and/or may be scaled in accordance the stimulation zone's intensity, as depicted at step 808.

At step 810, a determination is made with respect to whether there are any other stimulation zones to be placed. If there are additional stimulation zones, then the next strongest stimulation zone is placed by iterating through steps 800–808 again. During any subsequent iteration of these steps, electrodes, which have not already been activated, may be activated to produce stimulation corresponding to the stimulation zone currently being placed without taking into account any interaction between previously activated electrodes and the electrodes currently being activated.

Steps 812–818 are similar to 706–712 and 608–614 described above. If lead-location information is unavailable, then stimulation programming, via manipulation of electrode settings, may begin, as depicted at step 816, without displaying a depiction of the underlying physiology of the stimulatable area.

Figure 9:
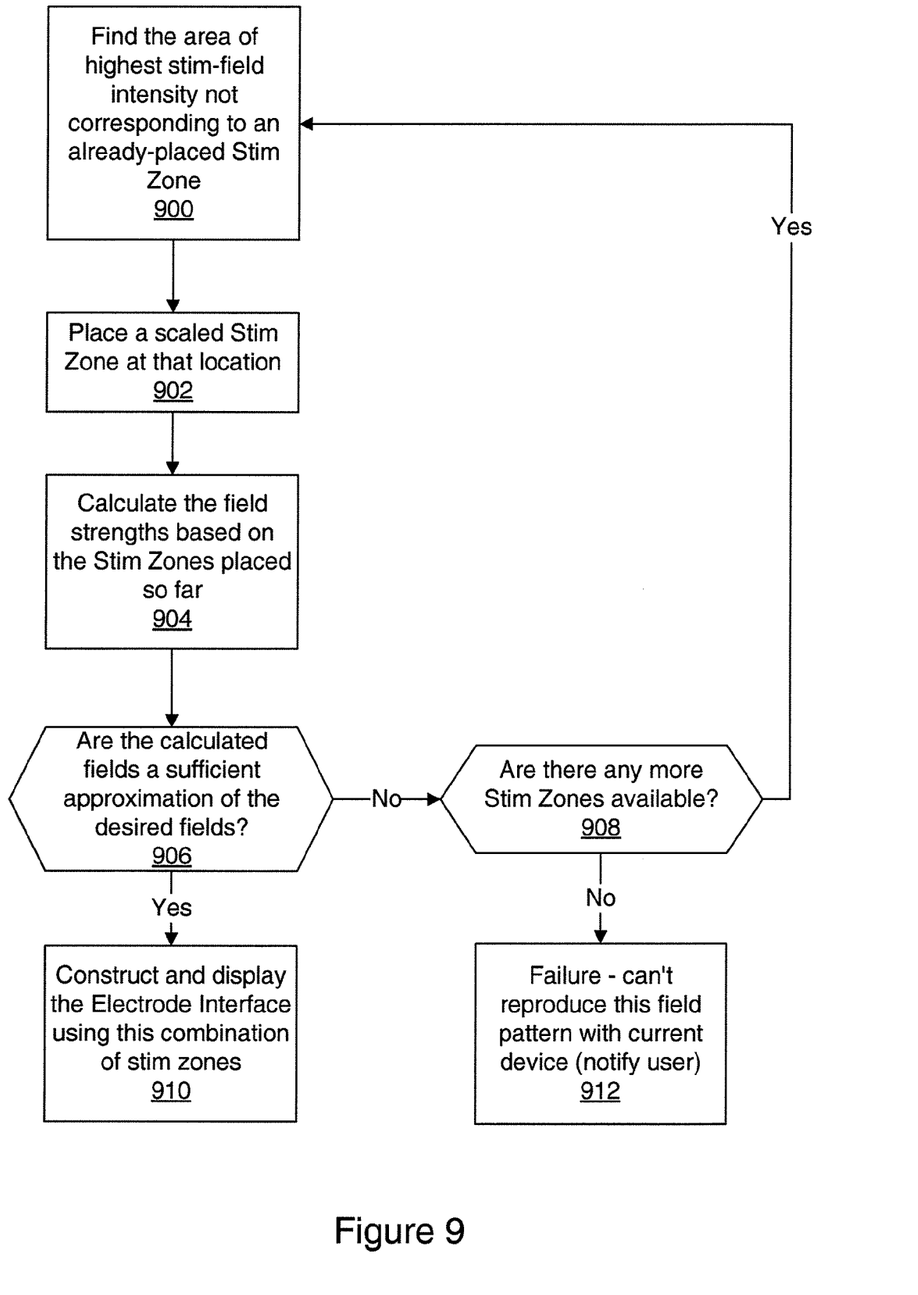
FIG. 9 depicts steps in accordance with an illustrative embodiment of the invention for transitioning from an electromagnetic fields-view representation of stimulation zones to an electrodes interface.

FIG. 9 shows steps in accordance with an illustrative embodiment of the invention for transitioning from an electromagnetic fields-view representation 300 of stimulation zones to an electrodes interface 400. The steps shown in FIG. 9 may be used, when an electromagnetic-fields representation is known, but a corresponding pattern of idealized stimulation zones is unknown. So, for instance, if a user defines electromagnetic fields initially without defining stimulation zones, or if a user makes significant changes, through the fields-view interface 300, to previously defined stimulation zones, the steps of FIG. 9 may be used to generate an approximation of a set of idealized stimulation zones that will produce the known electromagnetic-fields pattern.

FIG. 9 sets forth steps for generating a set of idealized stimulation zones via successive approximations. The steps in FIG. 9 find an area, which has the highest intensity among areas not corresponding to an already-placed stimulation zone, and place a stimulation zone in the found area, as depicted at steps 900 and 902. After placing a stimulation zone in this manner and as depicted at step 904, a field-strength pattern is calculated based on any stimulation zones that have already been placed.

Step 904 may be performed in a manner similar to the field-strength calculations described above in connection with steps 700–704 of FIG. 7.

Step 906 is essentially a metric for comparing how similar one field pattern is to another field pattern. If a calculated field pattern, which is based on the stimulation zones placed so far, is a sufficient approximation of the desired fields, then no more stimulation zones are placed, and an electrode interface 400 may be constructed and displayed, as depicted at step 910, using the stimulation zones placed in steps 900–906.

Otherwise, if any additional stimulation zones may be placed, then steps 908 and 900–906 are repeated for placing a next stimulation zone 204. The quality metric of step 906 may be weighted so that stronger areas of stimulation are given more importance by the quality metric. In this way, if the placed stimulation zones re-create the relatively stronger portions of the desired electromagnetic-field pattern, then the quality metric essentially doesn't care about the remaining relatively lower-intensity areas of the desired electromagnetic-field pattern. At steps 906, 908 and 912, if the calculated fields are an insufficient approximation of the desired fields and no more stimulation zones are available for placement, then an indication is provided to notify the user that the desired field pattern can not be reproduced with the IPG's current lead and electrode configuration.

The steps set forth in FIG. 9 will essentially generate idealized stimulation zones 204 based on a given pattern of desired electromagnetic-field strengths. The resulting stimulation zones 204 may then be used for constructing a stimulation-zones view 200 and/or an electrodes view 400.

What has been described above is merely illustrative of the application of the principles of the present invention. The invention should therefore be limited only by the claims below. Any of the methods of the invention may be implemented in software that may be stored on computer disks or other computer-readable media.

The invention claimed is:

1. A user interface for programming therapy settings of a neurostimulator having at least one stimulation lead implanted within a patient's body, each lead having a plurality of electrodes, the user interface comprising:
    a stimulation zone-programming interface that is at a first level of abstraction and that graphically displays, and allows a user to specify treatment parameters for, at least one idealized stimulation zone;
    a field strength-programming interface that is at a second level of abstraction lower than the first level of abstraction and that graphically displays, and allows a user to interact with, at least one modeled electromagnetic field strength representation corresponding to the at least one idealized stimulation zone; and
    an electrode-programming interface that is at a level of abstraction lower than the second level of abstraction and that displays, and allows a user to interact with, electrode settings.

2. The user interface of claim 1, wherein, to transition from the stimulation zone-programming interface to the field strength-programming interface, at least one electric field generated by the at least one stimulation zone is modeled as a point charge.

3. The user interface of claim 2, wherein, to transition from the field strength-programming interface to the electrode-programming interface, at least one idealized stimulation zone is mapped to electrode settings for at least one pair of electrodes near the idealized stimulation zone's location.

4. The user interface of claim 1, wherein, the stimulation zone-programming interface includes user-interface controls that allow a user to perform at least one stimulation zone-programming operation selected from the group of: creating, placing, moving, modifying, and deleting at least one idealized stimulation zone.

5. The user interface of claim 1, wherein, the field strength-programming interface includes user-interface controls that allow a user to perform at least one field strength-programming operation selected from the group of: creating, placing, moving, modifying, and deleting the at least one modeled electromagnetic field strength representation corresponding to the at least one idealized stimulation zone.

6. The user interface of claim 1, wherein, the electrode-programming interface includes user-interface controls that allow a user to perform at least one electrode-programming operation selected from the group of: creating, placing, moving, modifying, and deleting the electrode settings.

7. A computer-readable medium having computer-executable instructions that provide a user interface for programming therapy settings of a neurostimulator having at least one stimulation lead implanted within a patient's body, each lead having a plurality of electrodes, the computer-executable instructions performing steps comprising:
    receiving input specifying at least one treatment parameter for at least one idealized stimulation zone, wherein the at least one treatment parameter specifies a location of the at least one idealized stimulation zone, wherein the location is specified at a level of abstraction above indicating specific electrodes that should be activated; and
    generating electrode settings corresponding to the at least one idealized stimulation zone, wherein the electrode settings specify at least one pair of electrode-voltage levels based on the at least one treatment parameter.

8. The computer-readable medium of claim 7, having further computer-executable instructions that perform steps comprising: displaying, based on lead-placement information, a stimulation-zone view of a stimulatable area that is located near the at least one stimulation lead.

9. The computer-readable medium of claim 8, having further computer-executable instructions that perform steps comprising: displaying a representation of an underlying physiology of a region of the patient's body corresponding to the stimulatable area such that a user may position the at least one idealized stimulation zone relative to the displayed underlying physiology.

10. The computer-readable medium of claim 8, having further computer-executable instructions that perform steps comprising: superimposing on the displayed stimulatable area a depiction of discrete locations at which a user may place the at least one idealized stimulation zone.

11. The computer-readable medium of claim 10, wherein the depiction of discrete locations at which a user may place the at least one idealized stimulation zone is a grid of intersecting lines based on lead-placement and lead-configuration information.

12. The computer-readable medium of claim 8, having further computer-executable instructions that perform steps comprising: depicting the at least one idealized stimulation zone's location within the stimulation-zone view of the stimulatable area.

13. The computer-readable medium of claim 8, wherein the at least one treatment parameter includes at least one of the at least one idealized stimulation zone's treatment intensity, treatment rate, and treatment pulse width.

14. The computer-readable medium of claim 8, having further computer-executable instructions that perform steps comprising: providing user-interface controls that allow a user to modify the treatment parameters while the stimulation-zones view of the stimulatable area is being displayed.

15. The computer-readable medium of claim 7, having further computer-executable instructions that perform the step of generating the electrode settings for a specific one of the at least one idealized stimulation zone by performing further steps comprising: when the specific idealized stimulation zone is located proximate a first stimulation lead, selecting an electrode pair on the first stimulation lead, wherein a first electrode and a second electrode of the electrode pair are located closer to the specific idealized stimulation zone than any other electrodes on the first stimulation lead.

16. The computer-readable medium of claim 7, having further computer-executable instructions that perform the step of generating the electrode settings for a specific one of the at least one idealized stimulation zone by performing further steps comprising: when the specific idealized stimulation zone is located centrally between a first stimulation lead and a second stimulation lead, selecting an electrode pair that includes a first electrode from the first lead and a second electrode from the second lead.

17. The computer-readable medium of claim 7, having further computer-executable instructions that perform steps comprising: displaying an electrodes view depicting the electrode settings that correspond to the at least one idealized stimulation zone.

18. The computer-readable medium of claim 17, having further computer-executable instructions that perform steps comprising: providing user interface controls that allow the user to modify the treatment parameters while displaying the electrodes view of the stimulatable area.

19. The computer-readable medium of claim 7, having further computer-executable instructions that perform steps comprising: displaying an electromagnetic-fields view depicting at least one modeled electromagnetic field that corresponds to the at least one idealized stimulation zone.

20. The computer-readable medium of claim 19, having further computer-executable instructions that perform steps comprising: providing user interface controls that allow the user to modify the treatment parameters while displaying the electromagnetic-fields view of the stimulatable area.

21. A computer-readable medium having computer-executable instructions for generating and displaying a field strength-programming interface based on treatment-parameter information describing at least one stimulation zone, wherein the computer-executable instructions perform steps comprising:
modeling at least one stimulation-field strength corresponding to the at least one stimulation zone;
graphically displaying, within a representation of a stimulatable area, the modeled stimulation-field strength; and
providing user-interface controls that allow a user to specify treatment parameters, including treatment parameters pertaining to at least one of the at least one stimulation zone and the at least one stimulation-field strength.

22. The computer-readable medium of claim 21, having further computer-executable instructions that perform steps comprising: modeling each of the at least one stimulation zone as a respective point charge.

23. The computer-readable medium of claim 21, having further computer-executable instructions that perform steps comprising: scaling the intensity of each point charge according to an intensity of the corresponding respective stimulation zone.

24. The computer-readable medium of claim 21, having further computer-executable instructions that perform steps comprising: calculating the field strength for each displayed point within the displayed representation of the stimulatable area.

25. The computer-readable medium of claim 24, having further computer-executable instructions that perform the step of calculating the field strength for each displayed point within the representation of the stimulatable area by performing steps comprising: summing, at each displayed point within the representation of the stimulatable area, electric fields generated by each stimulation zone.

26. A computer-readable medium having computer-executable instructions for generating and displaying an electrode-programming interface based on treatment-parameter information describing a desired stimulation-field-strength pattern, wherein the computer-executable instructions perform steps comprising:

a. finding a location of highest stimulation-field intensity at which a stimulation zone has not yet been placed;

b. placing a scaled stimulation zone at the found location;

c. calculating, based on the stimulation zones placed so far, field strengths at various locations within a stimulatable area;

d. if the calculated field strengths are a sufficient approximation of the desired stimulation-field-strength pattern, generating and displaying the electrode-programming interface based on stimulation zones that have already been placed via step b; and e. if the calculated fields are an insufficient approximation of the desired fields, then:
if, based on the treatment-parameter information, additional stimulation zones can be placed at additional locations within the stimulatable area, repeating steps a through e,
if, based on the treatment-parameter information, additional stimulation zones are not available for placement within the stimulatable area, displaying a notification message stating that the field pattern cannot be reproduced.

27. A programming device for programming the therapy settings of the neurostimulator comprising: a user interface for programming therapy settings of a neurostimulator having at least one stimulation lead implanted within a patient's body, each lead having a plurality of electrodes, the user interface comprising: a stimulation zone-programming interface that is at a first level of abstraction and that graphically displays, and allows a user to specify treatment parameters for, at least one idealized stimulation zone; a field strength-programming interface that is at a second level of abstraction lower than the first level of abstraction and that graphically displays, and allows a user to interact with, at least one modeled electromagnetic field strength representation corresponding to the at least one idealized stimulation zone; and an electrode-programming interface that is at a level of abstraction lower than the second level of abstraction and that displays, and allows a user to interact with, electrode settings.

28. The programming device of claim 27, wherein, to transition from the stimulation zone-programming interface to the field strength-programming interface, at least one electric field generated by the at least one stimulation zone is modeled as a point charge; and to transition from the field strength-programming interface to the electrode-programming interface, at least one idealized stimulation zone is mapped to electrode settings for at least one pair of electrodes near the idealized stimulation zone's location.

* * * * *